(12) United States Patent
Darwish et al.

(10) Patent No.: US 8,768,674 B2
(45) Date of Patent: Jul. 1, 2014

(54) COMPUTER-IMPLEMENTED METHOD OF PREOPERATIVELY DETERMINING THE OPTIMIZED EXTERNAL SHAPE OF A PROSTHETIC FEMORAL HIP STEM

(71) Applicant: King Saud University, Riyadh (SA)

(72) Inventors: Saied Mohamed Hassan Darwish, Riyadh (SA); Mohamed Zoubir A. Bendjaballah, Riyadh (SA)

(73) Assignee: King Saud University, Riyadh (SA)

( * ) Notice: Subject to any disclaimer, the term of this patent is extended or adjusted under 35 U.S.C. 154(b) by 0 days.

(21) Appl. No.: 13/839,658

(22) Filed: Mar. 15, 2013

(65) Prior Publication Data

US 2013/0325430 A1    Dec. 5, 2013

(30) Foreign Application Priority Data

May 31, 2012  (EP) .................................... 12170166

(51) Int. Cl.
*G06F 17/50* (2006.01)
*G06G 7/48* (2006.01)
*A61F 2/30* (2006.01)
*A61F 2/28* (2006.01)

(52) U.S. Cl.
CPC ..... *A61F 2/30942* (2013.01); *A61F 2002/2825* (2013.01); *A61F 2002/2828* (2013.01); *A61F 2002/2832* (2013.01)
USPC ................................................. 703/11; 703/1

(58) Field of Classification Search
None
See application file for complete search history.

(56) References Cited

U.S. PATENT DOCUMENTS

| 4,506,393 A * | 3/1985 | Murphy ........................ 128/898 |
| 4,908,035 A * | 3/1990 | Deckner et al. ............ 623/23.15 |
| 8,078,440 B2 * | 12/2011 | Otto et al. ......................... 703/6 |
| 8,521,492 B2 * | 8/2013 | Otto et al. ......................... 703/6 |
| 2006/0276904 A1 | 12/2006 | Zweymuller ............... 623/22.11 |
| 2011/0282462 A1 | 11/2011 | Wunderle et al. .......... 623/23.35 |
| 2011/0288643 A1 * | 11/2011 | Linder-Ganz et al. ..... 623/14.12 |

FOREIGN PATENT DOCUMENTS

FR        2 674 744        10/1992
WO       WO 94/07439       4/1994

* cited by examiner

*Primary Examiner* — Omar Fernandez Rivas
*Assistant Examiner* — Nithya J Moll
(74) *Attorney, Agent, or Firm* — Jonathan M. D'Silva; MacDonald, Illig, Jones & Britton LLP

(57) ABSTRACT

Computer-implemented method of preoperatively determining the optimized external shape of a prosthetic femoral hip stem for use in partial cementing hip replacement procedures and of a reamer for reaming a cavity in the femur of a patient for implanting the prosthetic femoral hip stem, comprising: a) setting an initial external shape of the prosthetic femoral hip stem based on the reconstructed femur anatomy of a patient, b) generating an associated initial reamer by negatively offsetting the initial external shape of the prosthetic femoral hip stem by an uniform offset value δ, c) calculating contact stresses at the interface of the prosthetic femoral hip stem and the patient's femur when reamed by the initial reamer and d) optimizing the offset value δ, so that the contact stresses are within a predetermined acceptable range.

11 Claims, 5 Drawing Sheets

COMPUTER-IMPLEMENTED METHOD OF PREOPERATIVELY DETERMINING THE OPTIMIZED EXTERNAL SHAPE OF A PROSTHETIC FEMORAL HIP STEM

BACKGROUND

The present invention relates to a computer-implemented method of preoperatively determining the optimized external shape of a prosthetic femoral hip stem (implant) having a proximal and a distal segment as well as an intermediate segment between them, the proximal and distal segments to be press-fitted with an intramedullary canal of the femur of a patient and the intermediate segment having a reduced cross section for injecting cement, for use in partial cementing hip replacement procedures, and of a reamer for reaming a cavity in the femur of a patient for implanting the prosthetic femoral hip stem.

Accidents, bone disease and age cause damage to different human bones and joints, which leads to bones and joints being replaced or amended. All over the world several hundred thousands patients undergo surgeries for joints replacement or bone amendments due to accidents while several other thousands undergo implant operations due to age and bone diseases.

Everyone's bones are unique. They may be similar in size and shape, but the dimensions are different from patient to patient. Cemented implants were able to address these variations with only a few sizes, letting them "customize" the fit to the individual's bone. Without cement, it became much more difficult to address anatomical variations and still provide the required stability and contact. Most manufacturers of the cementless implants simply took a given design and made it larger or smaller to create a range of sizes. Unfortunately all patients are not built that way. The target market of the first custom made, however, traditional custom implants (i.e. in patients with tumors or trauma). If a patient has truly unique hip joint anatomy, doctors prefer the custom approach. In most revision cases they also prefer to use custom implants design. Custom-made implants up until this time were used mainly for tumor or trauma cases where a part is missing or badly misshapen.

The idea of custom-made cementless implants for the femur was developed. In this way a unique implant is made for each patient, thereby addressing the patients' individual anatomic variations. The challenge is to manufacture an implant accurately and without too much additional cost. The tailor-made implants could prove more durability over a wider range of motion for patients.

In presence of marked deformities, custom made prostheses may be the only viable solution. When compared with standard cementless design, custom-made prostheses seem to achieve better contact at the bone-implant interface leading to the least stress shielding.

Unfortunately bone quality for hip replacement patients are not the same (tumor and bone diseases). So, part of the patient bones (high quality) could withstand the cementless technique, while the rest (bad quality) could only withstand the cemented hip technique.

In view of this, hybrid-segmented or (tri-compartmental) hip implants (prosthetic femoral hip stems) were developed. Such a hip implant comprises a proximal and a distal segment and an intermediate segment between them. The proximal and distal segments of the implant are manufactured so as to provide a press-fit with the patients' intramedullary canal. In contrast the intermediate segment is provided with a reduced cross section so as to create a clearance between the implant and the bone. Thereby the implant can be cemented to the patients' bone in the intermediate section.

SUMMARY

It is an objective of the present invention to provide a method of optimizing the design of a prosthetic femoral hip stem having a proximal and a distal segment as well as an intermediate segment between them, the proximal and distal segments to be press-fitted into an intramedullary canal of the femur of a patient and the intermediate segment having a reduced cross section for injecting cement, for use in partial cementing hip replacement procedures.

This objective is achieved with a computer-implemented method of preoperatively determining the optimized external shape of a prosthetic femoral hip stem having a proximal and a distal segment as well as an intermediate segment between them, the proximal and distal segments to be press-fitted with an intramedullary canal of the femur of a patient and the intermediate segment having a reduced cross section for injecting cement, for use in partial cementing hip replacement procedures and of a reamer for reaming a cavity in the femur of a patient for implanting the prosthetic femoral hip stem, comprising: a) setting an initial external shape of the prosthetic femoral hip stem based on the reconstructed femur anatomy of a patient, b) generating an associated initial reamer by negatively offsetting the initial external shape of the prosthetic femoral hip stem by a preferably uniform offset value $\delta$, c) calculating contact stresses at the interface of the prosthetic femoral hip stem and the patient's femur when reamed by the initial reamer and d) optimizing the offset value $\delta$, so that the contact stresses are within a predetermined acceptable range for promotion of bone formation and fast and preferably full osseointegration, by shrinking the prosthetic femoral hip stem and/or the reamer as required. A negative offset refers to a uniform shrink applied to the external shape of the implant, which a positive offset produces a surface based on a uniform enlargement of the same surface.

Preferably the optimizing step d) is also carried out with regard to the prosthetic femoral hip stem pull out force.

Advantageously, the optimizing step d) comprises the following iteration steps: if the calculated contact stresses are above the acceptable range, decreasing the offset value $\delta$ by shrinking the prosthetic femoral hip stem and calculating contact stresses at the interface of the shrinked prosthetic femoral hip stem and the patient's femur when reamed by the reamer, and if the calculated contact stresses are below the acceptable range, increasing the offset value $\delta$ by shrinking the reamer and calculating contact stresses at the interface of the prosthetic femoral hip stem and the patient's femur when reamed by the shrinked reamer.

According to one contemplated embodiment the setting step a) comprises: acquiring a CT-scan of the pelvis and the femur of the patient, and developing of a 3D-solid model of the initial prosthetic femoral hip stem.

For example, the generating b) could comprise: generating a CAD surface model of the associated reamer to carry out a Boolean operation intended for simulating cancellous bone reaming.

Also, the calculating step c) could comprise: extracting the cortical and cancellous bone layers, preferably by using a medical image editor software, for example MIMICS 14.0©, and preferably by creating a finite element mesh for each bone layer for estimating the bone material properties based on the element bone density represented by the average pixel's Hounsfield unit.

Conveniently, before calculating the contact stress a head and a neck are provided to the prosthetic femur hip stem.

Finally, preferably the calculating step is performed using finite element analysis, for example the FE package (ABAQUS).

The invention recognizes that by way of numerical modelling of contact stresses at the bone-implant interface and/or the implant pull out force the shape/design of a prosthetic femoral hip stem as well as of an associated reamer can be optimized simultaneously/in parallel. In particular, the design of a tri-compartmental, hybrid, hip implant as well as its associated/corresponding reamer can be optimized. Both the shape of the implant (patient specific) and the type of the implant (hybrid and tri-compartmental) are addressed by the invention. The most distal and proximal segments of the hip stem are shrink-fitted/press-fitted, while the segment in the middle is cemented. The amount of clearance/interference is optimized through a numerical procedure.

BRIEF DESCRIPTION OF THE DRAWINGS

Further features and advantages of the invention can be gathered from the following description of a special embodiment with reference to the attached diagrammatic drawings, in which.

DETAILED DESCRIPTION

Figure 1:
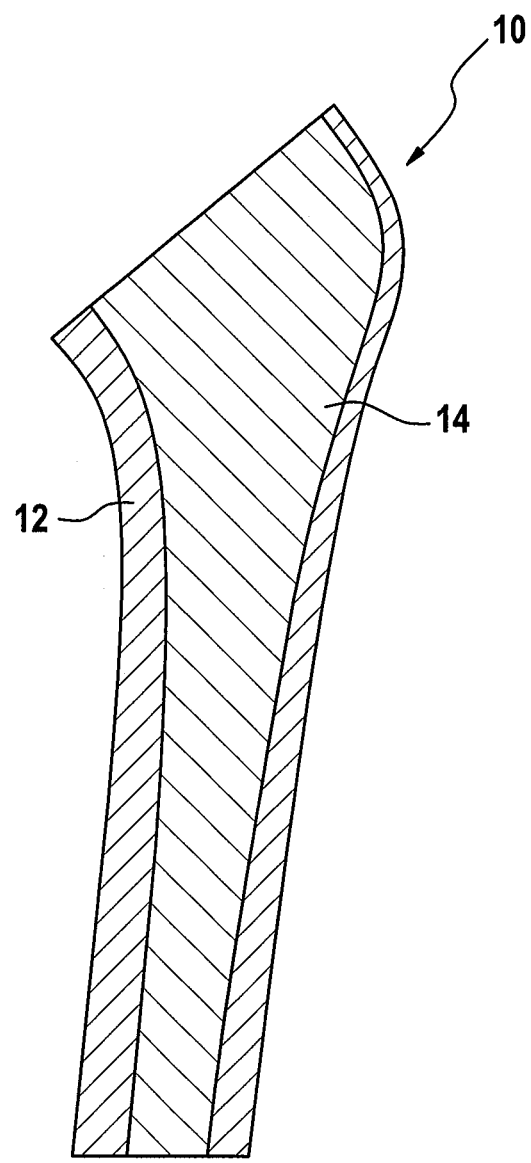
FIG. 1 shows a frontal plane sectioned model of a patient's femur showing the cancellous and cortical bone layers.

Hereinafter a description of a computer-implemented method, shown in FIG. 5, according to a special embodiment of the present invention will follow:

Diseased bones comprise cancellous and cortical bone layers. Models of cortical and cancellous bone layers are reconstructed using CT-scan of the patients pelvis and femur 10 (see FIGS. 1 and 5) and by way of a subsequent segmentation carried out using a specific threshold that helps to isolate both the outer cortical as well as the inner cancellous bone layers 12 and 14 (see FIG. 1) a 3D-solid model of an initial prosthetic femoral hip stem is developed (see FIG. 5).

Figure 2:
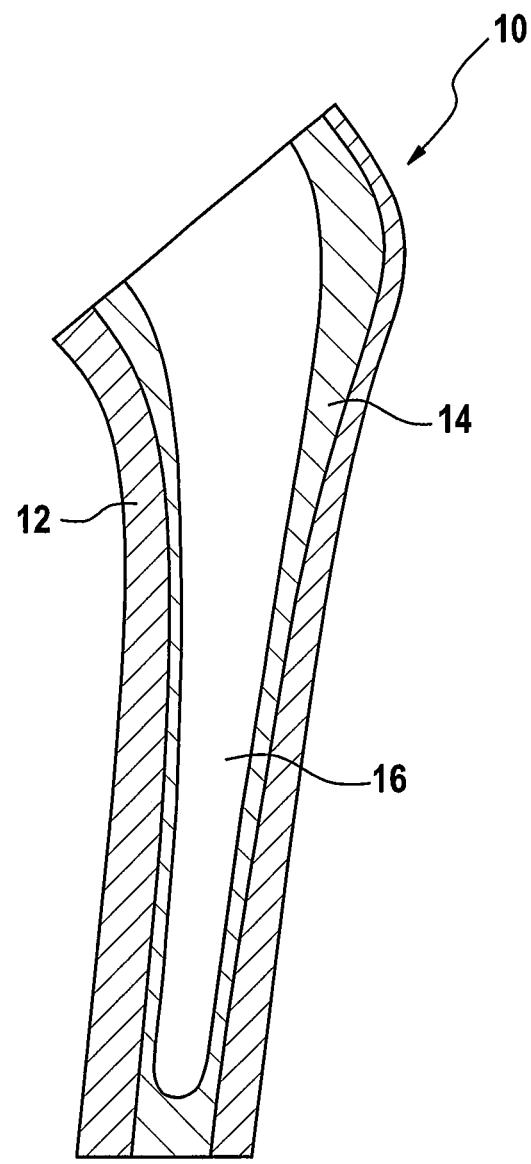
FIG. 2 shows a frontal plane sectioned model of the femur of FIG. 1 showing the hollowed cancellous bone reamed by a reamer.
Figure 5:
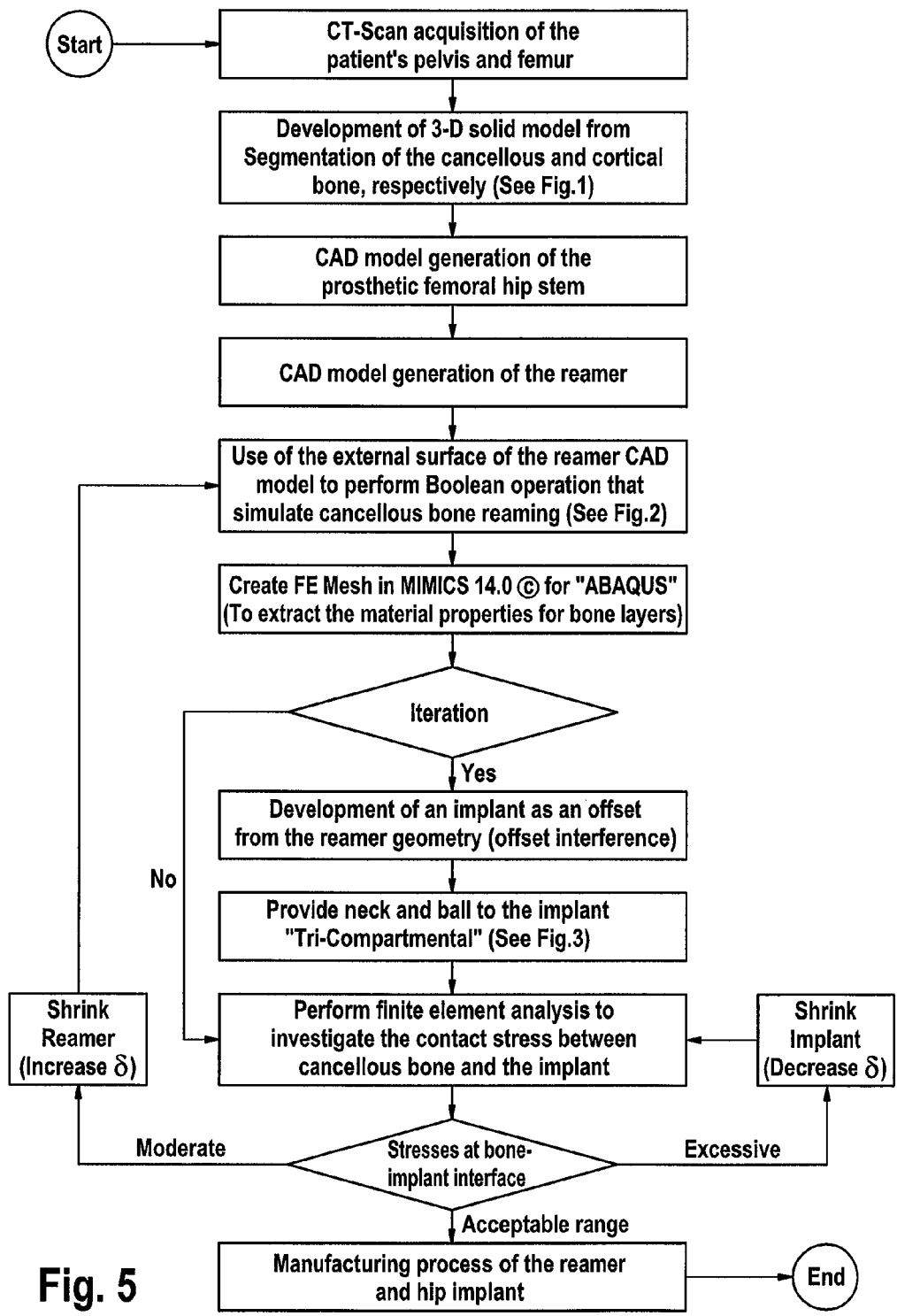
FIG. 5 shows a flow chart showing a computer-implemented method according to a contemplated embodiment of the present invention.

Furthermore, according to FIG. 5, then an associated initial reamer (not shown) is generated by way of a surface CAD-model. Subsequently, a Boolean operation is used to simulate cancellous bone reaming by way of said associated initial reamer (see FIGS. 5 and 2). FIG. 2 shows a frontal plane sectioned model of the femur showing the hollowed cancellous bone or bone layer using said associated initial reamer. The reamer print is labeled as 16 and consists in a cavity reamed by said reamer. In other words, when the preliminary shape of the implant stem is generated to constitute the reamer geometry, the surface thereof is used to simulate the hollowing or reaming operation of the bone named Boolean operation.

Then, according to FIG. 5, a mesh is created for the finite element software "ABAQUS" for extracting the material properties of the bone layers. Considering the bone material as linear elastic homogeneous and isotropic (LEHI), the material properties of each bone layer are directly extracted from the software, making use only of the pixels enclosed in the mask in question. A known correlation between the pixel grey value or the "Hounsfield unit" and the density is used to compute the material's local density. Then a correlation linking the bone density to the modulus of elasticity and Poisson's ratio is performed to end up with averaged values of the material properties for the considered layers only.

Figure 3:
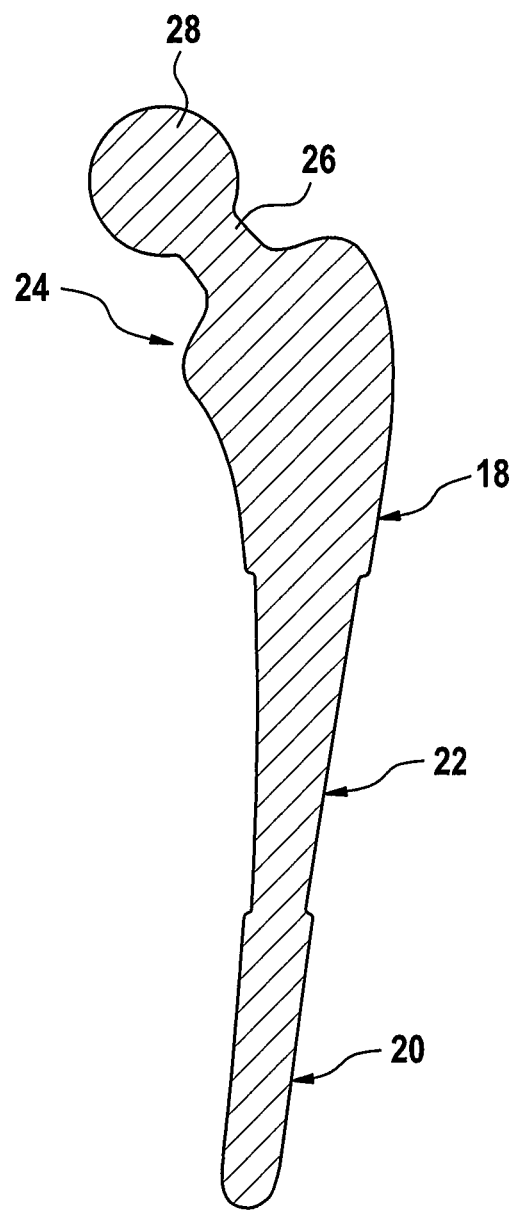
FIG. 3 shows a 3D-CAD-model of a prosthetic femoral hip stem (tri-compartmental hybrid hip implant) obtained as an offset from a reamer model further modified to include the femoral head and the middle neck region that would house injectable acryl cement layer.

Thereafter an iteration starts (see FIG. 5). An implant (prosthetic femoral hip stem 24) as an offset from the reamer geometry (offset=interference) is developed. Further a neck 26 and a ball (femoral head 28) is provided to the prosthetic femoral hip stem 24 so that a "tri-compartmental" hip implant results (see FIG. 3).

Then a finite element analysis is performed to investigate the contact stress between the cancellous bone and the implant. If the stresses at the bone-implant interface are excessive, that means above a stress shielding interval which represents the ideal stress values referred to as the "acceptable range" of stresses that best promote bone formation and hence ensures fast and full osseointegration with the implant, the implant is shrinked by way of decreasing an offset value $\delta$ representing the interference that would occur after reaming operation between the bone and the implant (see FIG. 5), in other words, the uniform offset between a prosthetic implant and its corresponding reamer. If the stresses at the bone-implant interface are moderate, i. e. below the stress shielding interval, the reamer is shrinked by increasing $\delta$ (see FIG. 5). In the latter case an even lesser amount of bone removal results.

If the stresses should be within said stress shielding interval or acceptable range, the iteration ends (see FIG. 5).

Figure 4:
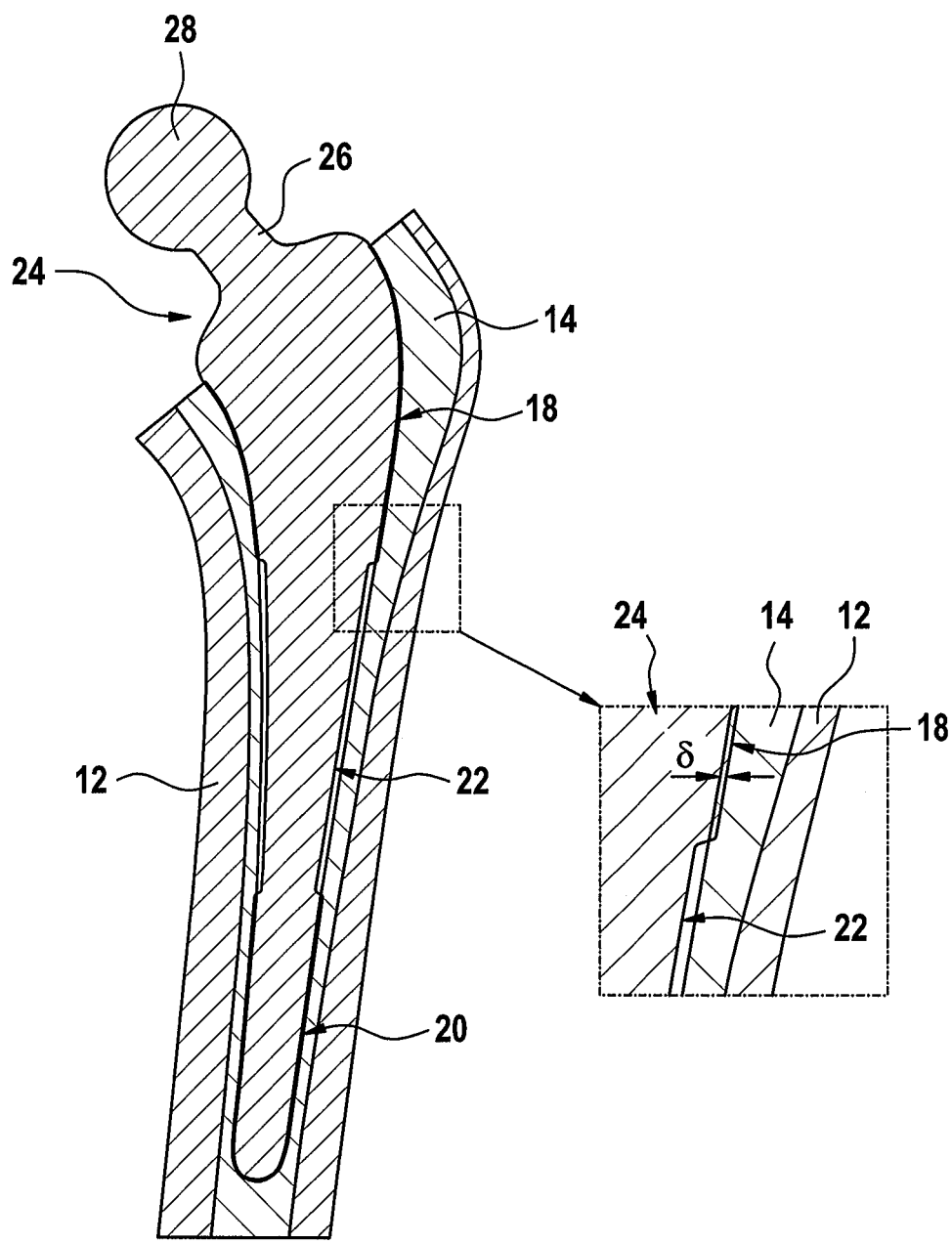
FIG. 4 shows the femoral hip stem of FIG. 3 inside the femur of FIG. 2.

FIG. 4 is for the sake of completeness. It shows that the tri-compartmental hip implant (hip stem 24) interferes with bone in its most proximal 18 and most distal segment 20, respectfully, while an intermediate segment 22 of the implant to be cemented presents a clearance. The internal surface of the intramedullary canal is reproduced from CT or MR data. Some contours from the intramedullary region are selected and used as a framework for the femur stem shape development. In this step, contours from the most proximal segment 18 and distal segment 20 are offset to increase the cross-sectional areas of the hip stem to make the hip implant interfere with bone while in the intermediate segment 22 the contours are shrank to create a clearance between the stem and the bone. Both distal segment 20 and proximal segment 18 provide a retention area to the cement injected in the implant's intermediate segment.

In the specific example described above, the offset $\delta$ refers to both proximal and distal femoral stem segments and does not include the intermediate segment. The offset is chosen as constant. However, a variable offset could be also used by assigning increasingly more interference with the femoral stem depth leading to more offset values in the distal segment compared to its proximal counterpart. Such an approach would permit, eventually and if needed, a more equitable contributions of both segments to pull out for us exerted on the femoral.

Since diseased bones are of mixed quality, a hybrid-segmented hip implant should help doctors to take advantage of cementless hip replacements for high bone quality and cemented technique for low bone quality. This will be judged based on CT scan of the patient.

The features in the foregoing description, in the claims and/or in the accompanying drawings may, both and in any combination thereof, be material for realising the invention in diverse forms thereof. It is contemplated that many modifications can be made to the invention as shown and described in the drawings and description herein without departing from the contemplated scope of the claims.

The invention claimed is:

1. A computer-implemented method of preoperatively determining an optimized external shape of a prosthetic femoral hip stem having a proximal and a distal segment as well as an intermediate segment between them, the proximal and distal segments to be press-fitted with an intramedullary canal of a femur of a patient and the intermediate segment having a reduced cross section for injecting cement, for use in partial cementing hip replacement procedures and of a reamer for reaming a cavity in the femur of a patient for implanting the prosthetic femoral hip stem, the method comprising:
    a) setting an initial external shape of the prosthetic femoral hip stem based on a reconstructed femur anatomy of a patient;
    b) generating an associated initial reamer by negatively offsetting the initial external shape of the prosthetic femoral hip stem by a offset value $\delta$;
    c) calculating contact stresses at an interface of the prosthetic femoral hip stem and the patient's femur when reamed by the initial reamer; and
    d) optimizing the offset value $\delta$, so that the contact stresses are within a predetermined acceptable range for promotion of bone formation and osseointegration, by shrinking the prosthetic femoral hip stem and/or the reamer as required.

2. The method of claim 1 further comprising optimizing said offset value $\delta$, by shrinking the prosthetic femoral hip stem and/or the reamer as required, with regard to the prosthetic femoral hip stem pull out force.

3. The method of claim 1 further comprising optimizing said offset value $\delta$, by shrinking the prosthetic femoral hip stem and/or the reamer as required, wherein:
    if the calculated contact stresses are above said predetermined acceptable range, decreasing the offset value $\delta$ by shrinking the prosthetic femoral hip stem and calculating contact stresses at the interface of the shrinked prosthetic femoral hip stem and the patient's femur when reamed by the reamer; and
    if the calculated contact stresses are below said predetermined acceptable range, increasing the offset value $\delta$ by shrinking the reamer and calculating contact stresses at the interface of the prosthetic femoral hip stem and the patient's femur when reamed by the shrinked reamer.

4. The method of claim 1 wherein said setting an initial external shape of the prosthetic femoral hip stem based on the reconstructed femur anatomy of a patient comprises:
    acquiring a CT-scan of a pelvis and the femur of the patient; and
    developing a 3D-solid model of the initial prosthetic femoral hip stem.

5. The method of claim 4 wherein said generating an associated initial reamer by negatively offsetting the initial external shape of the prosthetic femoral hip stem by a preferably uniform offset value $\delta$ comprises generating a CAD surface model of the associated reamer to carry out a Boolean operation intended for simulating cancellous bone reaming.

6. The method of claim 5 wherein said calculating contact stresses at the interface of the prosthetic femoral hip stem and the patient's femur when reamed by the initial reamer comprises:
    extracting cortical and cancellous bone layers.

7. The method of claim 6, wherein extracting the cortical and cancellous bone layers is performed by using a medical image editor software.

8. The method of claim 6 wherein extracting the cortical and cancellous bone layers is performed by creating a finite element mesh for each bone layer for estimating the bone material properties based on an element bone density.

9. The method of claim 8 wherein creating said finite element mesh for each bone layer for estimating the bone material properties based on said element bone density is represented by the average pixel's Hounsfield unit.

10. The method of claim 1 further comprising providing a head and neck to the prosthetic femoral hip before calculating contact stress at the interface of the prosthetic femoral hip stem and the patient's femur.

11. The method of claim 1 further comprising performing a calculating step before using finite element analysis.

* * * * *